(12) United States Patent
Peterson et al.

(10) Patent No.: US 6,641,599 B2
(45) Date of Patent: Nov. 4, 2003

(54) SYSTEMS OF THERAPEUTIC TREATMENT

(75) Inventors: Kimberly K. Peterson, Peyton, CO (US); Douglas B. Peterson, Peyton, CO (US)

(73) Assignee: D & K Unlimited, Inc., Elizabeth, CO (US)

( * ) Notice: Subject to any disclaimer, the term of this patent is extended or adjusted under 35 U.S.C. 154(b) by 0 days.

(21) Appl. No.: 10/014,847

(22) Filed: Oct. 26, 2001

(65) Prior Publication Data

US 2003/0083720 A1 May 1, 2003

(51) Int. Cl.$^7$ ............................................. A61N 5/067
(52) U.S. Cl. ..................... 607/88; 128/898; 128/907; 607/89
(58) Field of Search ........................... 607/88; 600/548; 128/907, 898

(56) References Cited

U.S. PATENT DOCUMENTS

| | | | |
|---|---|---|---|
| 1,730,808 A | 10/1929 | Croom | |
| 4,535,784 A | 8/1985 | Rohlicek et al. | 128/735 |
| 4,622,972 A | 11/1986 | Giebeler, Jr. | 128/399 |
| 4,653,495 A | 3/1987 | Nanaumi | 128/303.1 |
| 4,825,868 A | 5/1989 | Susa et al. | 128/376 |
| 4,831,504 A | 5/1989 | Nishizawa et al. | 362/100 |
| 4,917,084 A | 4/1990 | Sinofsky | 606/7 |
| 5,000,752 A | 3/1991 | Hoskin et al. | 606/9 |
| 5,024,236 A | 6/1991 | Shapiro | 128/735 |
| 5,178,617 A | 1/1993 | Kuizenga et al. | 606/17 |
| D333,351 S | 2/1993 | Tsou | D24/206 |
| 5,199,876 A * | 4/1993 | Waldman | 434/262 |
| 5,250,068 A | 10/1993 | Ideguchi et al. | 606/189 |
| 5,259,380 A | 11/1993 | Mendes et al. | 607/115 |
| 5,300,097 A | 4/1994 | Lerner et al. | 607/93 |
| D347,283 S | 5/1994 | Von Winckler | D24/214 |
| 5,358,503 A | 10/1994 | Bertwell et al. | 606/27 |
| 5,413,587 A | 5/1995 | Hochstein | 607/100 |
| 5,417,706 A * | 5/1995 | Chun | 606/189 |
| 5,420,768 A | 5/1995 | Kennedy | 362/119 |
| 5,643,173 A | 7/1997 | Welles | 600/26 |
| 5,779,483 A * | 7/1998 | Cho | 434/262 |
| 5,843,074 A | 12/1998 | Cocilovo | 606/10 |
| 5,950,635 A * | 9/1999 | Garcia-Rill et al. | 128/898 |
| 6,019,482 A | 2/2000 | Everett | 362/184 |
| 6,074,411 A * | 6/2000 | Lai et al. | 607/89 |
| 6,238,424 B1 | 5/2001 | Thiberg | 607/88 |
| 6,238,425 B1 | 5/2001 | Thiberg | 607/88 |
| 6,267,721 B1 * | 7/2001 | Welles | 600/26 |
| 6,267,780 B1 | 7/2001 | Streeter | 607/89 |
| 2002/0007835 A1 * | 1/2002 | Otte | 128/898 |

OTHER PUBLICATIONS

Principles and Practice of Contemporary Acupuncture by Sung J. Liao, Mathew H. M. Lee and Lorenz K. Y Ng, published in 1994 by Marcel Dekker, Inc.*

Acupuncture, The Past and the Present by Kee Chang Huang, published by Vantage press, Inc, 1996.*

* cited by examiner

Primary Examiner—Roy D. Gibson
Assistant Examiner—H M. Johnson
(74) Attorney, Agent, or Firm—James R. Young; Faegre & Benson LLP

(57) ABSTRACT

A system and method of therapeutic treatment of an individual by applying a therapeutic modality to a plurality of therapeutic systems of the body. A plurality of therapeutic points of the therapeutic systems are stimulated and the body is therapeutically treated in response to such stimulation. Embodiments may provide applying at least one therapeutic light modality to each of a plurality of a plurality of therapeutic systems of an individual and stimulating a plurality of therapeutic points of each of the therapeutic systems. The individual is therapeutically treated in response to the stimulation. Embodiments may also provide applying a plurality of therapeutic modalities comprising at least one visible light modality and an infrared light modality to at least one therapeutic microsystem of the individual and stimulating a plurality of therapeutic points of the therapeutic microsystem. The individual is therapeutically treated in response to the stimulation.

66 Claims, 2 Drawing Sheets

SYSTEMS OF THERAPEUTIC TREATMENT

BACKGROUND OF THE INVENTION

The present invention relates generally to the field of therapeutic treatment of an individual and the treatment of therapeutic systems of the body. Specifically, the present invention may relate to the therapeutic treatment of an individual through body therapeutic modalities and therapeutic systems, such as acupuncture, acupressure and meridian systems of the body, and therapeutic microsystems. The invention may be especially applicable to therapeutic treatment of therapeutic points of the body, such as reflexology points and points such as acupressure, acupuncture, and meridian points, and may also provide for the treatment of one or a plurality therapeutic systems. The invention may also be especially applicable for the provision and treatment through one, several, or a plurality of therapeutic modalities, such as light. The invention may find application for the relief of many common ailments and disorders, such as muscle relaxation, muscle and joint pain, muscle spasm, stiffness, arthritis, and abdomen and intestinal illness, among others.

Acupuncture and acupressure are well-known therapies that have been practiced in many disciplines. Research has been building that may establish the effectiveness of acupuncture and acupressure to relieve pain and to promote healing and improve functioning. The insertion of needles, application of heat, and application of electrical stimulation at very precise acupuncture points is a common practice to achieve these benefits. Furthermore, the therapeutic treatment of the body has undergone various technological and procedural changes, especially in the various therapies currently practiced by present day practitioners. For example, acupuncture, acupressure, and reflexology, among other therapies, may be conducted to identify bodily areas of concern, such as an injured or ailing body part or portion thereof.

Therapies such as acupressure, acupuncture, and reflexology, have also been heretofore practiced for relieving localized and determined pain, as previously described. These therapies may be carried out through modalities such as needle insertion, electrical stimulation, pressure, heat, light, ultrasound or other such treatment, and may have been directed to particular points of the body to treat a specific body part of concern, or portion thereof, either through direct application to the body part or through application to representative therapeutic system points of the body part.

One traditional view in acupuncture, acupressure, and reflexology describes the body as a network of meridians or energy channels that pass through the body and its surface to form meridian systems. Therapeutic points along the meridians may be stimulated, and in some applications unblocked, by various modalities to achieve healthful results potentially for a specific body part of concern, or portion thereof. One modern view may describe such therapies as providing the stimulation of points to provide a response from the nervous system to potentially provide a therapeutic reaction, such as the release of chemicals in the body for the treatment of a specific body part of concern, or portion thereof.

Therapies may have historically provided for the identification and treatment of an area of concern, such as a body part or portion thereof, through the stimulation of particular therapeutic points of a therapeutic system. Such therapies may be considered an alternative or supplement to traditional forms of pharmacological treatment, for example, the application of anti-inflammatory drugs such as aspirin or ibuprophin. Therapies directed to therapeutic systems and therapeutic points thereof, such as acupuncture, acupressure, and reflexology, traditionally have been viewed as desirable alternatives to medicinal therapy which may have undesirable effects to the body and can be costly, among other characteristics. However, the identification or treatment of a particular body part or portion thereof, may not be the most efficient mode of treatment, especially when an area of concern has not been identified or when a more generalized therapy is preferred. Injury of one area or body part, for example, may create compensation effects in other areas or parts of the body, potentially creating additional stress, strain, injury, or other undesirable body condition that may not be addressed through previous therapeutic efforts directed to only particular body parts or a bodily area of concern. Therefore, a recognized need exists for a therapeutic treatment for the body, as an alternative to medicinal therapy. Furthermore, a recognized need may exist for a more encompassing therapeutic treatment of the body, apart from past attempts in the above mentioned therapies, that may have only addressed particular bodily areas of concern, such as a body part or portion thereof.

The stimulation of particular points of the body, potentially representative of a body part, or particular points of a therapeutic system, may be provided in therapeutic treatment such as reflexology. Reflexology may provide treatment modalities to therapeutic points of the body or reflexology points, such as acupuncture, acupressure and meridian points. The stimulation of these points may be carried out by modalities such as needle insertion, electrical stimulation, pressure, heat, light, ultrasound or other such treatment. The points, as previously mentioned, may be part of a therapeutic system of the body, such as a therapeutic microsystem representative of the body. For example, the ear may be considered a therapeutic system, and may be considered a therapeutic microsystem of the body whereby specific therapeutic points of the ear may represent a specific body part, or portion thereof, of an individual. The hands and feet may also provide therapeutic systems, and may provide therapeutic microsystems. A therapeutic microsystem may be considered a portion of the body that provides therapeutic points reflecting the whole body.

Reflexology treatment has heretofore provided for treatment through therapeutic systems; however, practitioners may not have understood the interrelatedness and benefits of the treatment based upon a therapeutic system, a plurality of therapeutic systems, and in some therapies as disclosed herein, the treatment of one or a plurality of therapeutic microsystems, or in some instances, the subsequent treatment of bodily areas of concern. For example, a traditional view has been that reflexes in the hands were not as easily stimulated as those in the feet, and, therefore, a less effective result may have been believed to be obtained through hand reflexology. Previous practice in reflexology, therefore, could be construed as having taught away from the treatment of a plurality of therapeutic systems, potentially and particularly, the treatment of a plurality of therapeutic microsystems, as provided in embodiments of the present invention. Furthermore, conventional reflexology treatment modalities lacked the more encompassing treatment of the body of an individual according to the present invention, which includes the general treatment of the body followed by treatment of a bodily area of concern.

Furthermore, light therapy traditionally provided a modality for therapeutic application to therapeutic system points, potentially achieving stimulation of particular points. Some systems have incorporated coherent light, such as lasers, as the therapy modality. While potentially achieving desirable results for therapeutic point stimulation, the use of lasers is costly and may require undesired control limitations of the laser energy, among other undesirable characteristics. Other therapeutic light modalities have been used, such as non-coherent light, provided by devices incorporating light-emitting diodes (LEDs) or other such elements for visible light application, including infrared light.

While traditional therapeutic practice may have provided for treatment through a particular modality, such as light, and the application of the modality either directly to the identified area of concern or to particular points of a therapeutic system or microsystem to treat a specific body part or portion thereof, as disclosed in U.S. Pat. Nos. 6,238,424, 6,238,425, 5,250,068 and 5,843,074, such practices fail to identify or recognize therapeutic modalities that are more encompassing of treatments of the body, and including treatments specifically directed to treatment through the therapeutic system, such as a therapeutic microsystem, as opposed to particular points thereof, and the treatment of a plurality of therapeutic systems. The conventional techniques of the cited art further fail to recognize therapeutic treatments for the body, and subsequent treatment of bodily areas of concern. These conventional systems further lack in understanding of the treatment of the body and subsequent treatment of a bodily area of concern. Such attempts, therefore, did not address needs for more encompassing therapeutic treatment of the body.

Although such previous attempts may identify application of therapeutic treatment through stimulation of therapeutic points, and even through the use of light modalities, such efforts, as in other efforts previously mentioned, may actually teach away from the features and benefits provided by therapeutic treatment directed to the body and applied to therapeutic systems and microsystems, in accordance with embodiments of the present invention.

SUMMARY OF THE INVENTION

The present invention is designed to address the potential problems associated with conventional therapeutic treatment. Accordingly, embodiments of the present invention may provide for systems and methods of therapeutic treatment that address inadequacies of previous techniques.

The present invention comprises a method of therapeutic treatment of an individual, including applying a therapeutic modality to a plurality of therapeutic systems of the body; stimulating a plurality of therapeutic points of the plurality of therapeutic systems representative of the body; and therapeutically treating the body in response to such stimulation. A method of therapeutic treatment of an individual, may also be provided in accordance with the present invention as comprising applying at least one therapeutic light modality to each of a plurality of therapeutic systems of an individual; stimulating a plurality of therapeutic points of each of the plurality of therapeutic systems; and therapeutically treating the individual in response to the stimulation. Additionally, in accordance with the present invention, a method of therapeutic treatment of an individual comprises applying a plurality of therapeutic modalities comprising at least one visible light modality and an infrared light modality to at least one therapeutic microsystem of the individual; stimulating a plurality of therapeutic points of the at least one therapeutic microsystem; and therapeutically treating the individual in response to stimulation.

DETAILED DESCRIPTION OF PREFERRED EMBODIMENTS

The basic concepts of the invention may be embodied in many different ways. The inventive concept may involve the materials, elements, apparatus, device and methods for therapeutic treatment, and in preferred embodiments, therapeutic treatment of an individual or the body thereof.

Figure 1:
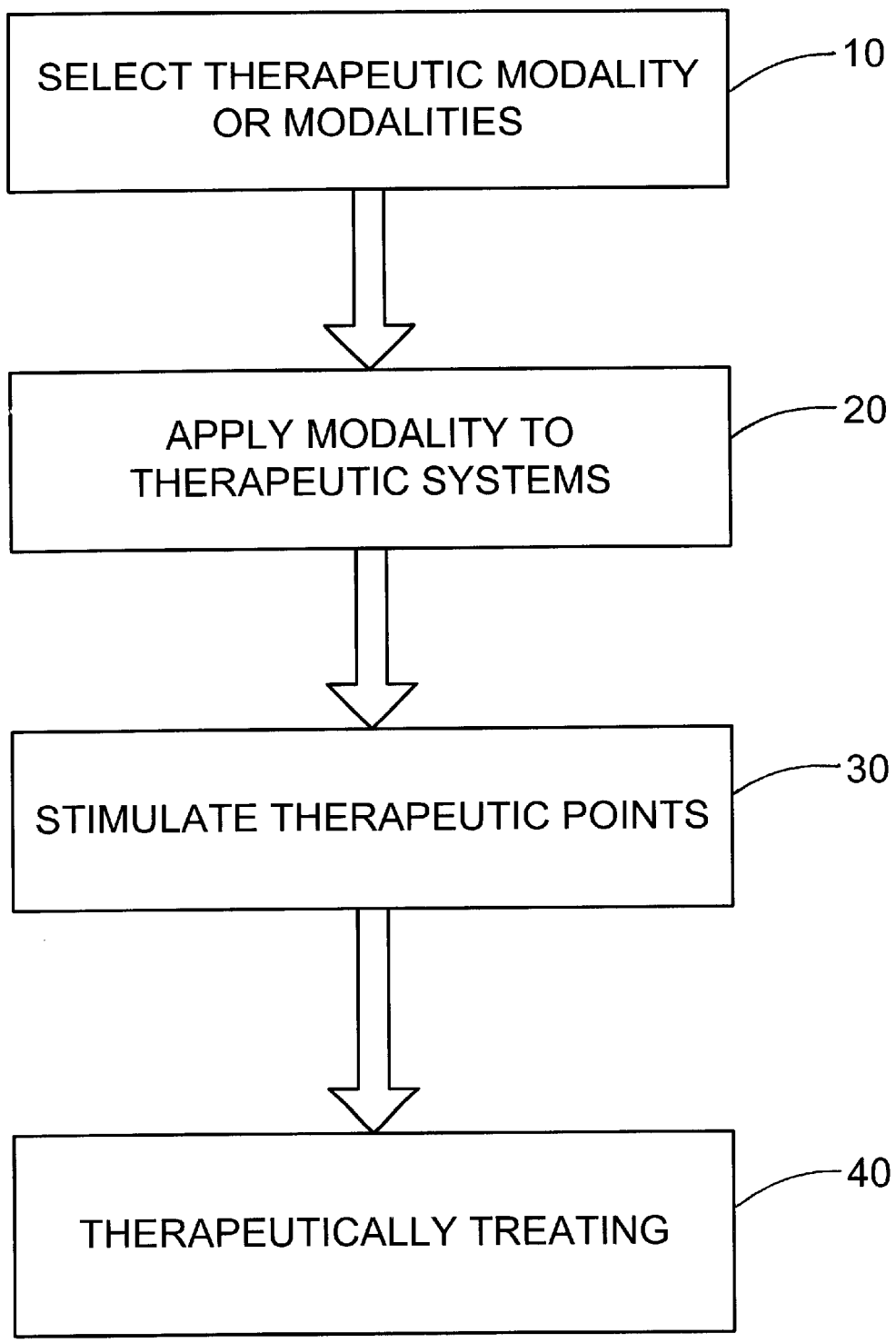
FIG. 1 is a diagrammatic representation of an embodiment of the present invention.

One embodiment of the present invention is provided in FIG. 1. The procedure for the therapeutic treatment of the body of an individual is described in steps, wherein a therapeutic modality is determined (10) to achieve the proper therapy. For example, a therapeutic modality, or a plurality of modalities, may be selected from known therapies such as acupressure, acupuncture, reflexology, and may include ultrasound, light, or heat, as applied in embodiments of the present invention, and in accordance with the individual's determined therapeutic need.

Furthermore, therapeutic modalities may be selected for features indicative of therapeutic application, such as abdomen, a colic valve, and whole body therapeutic, among other therapeutic applications. For example, practitioners have recognized that many illnesses, allergies, infections, diseases and disorders may have a start in the intestines of individuals. The intestines may become clogged, leaky, toxic, diseased, etc., by what and how the individual eats and by how poorly wastes are eliminated, and the body may be unable to properly absorb nutrients, potentially nutrients for healing. The colic valve (ileocecal valve) may prevent reflux from the cecum or large intestine from leaking into the ileum or small intestines, and may act as a sphincter to prevent the contents of the ileum from passing quickly into the cecum. The colic valve is believed to have the potential of operating abnormally. Embodiments of the present invention, especially those providing light modalities, incorporating application to the abdomen or the colic valve, can have a stimulating and calming effect that may induce or restore proper function of the colic valve. This therapeutic result is believed to result from the biomodulation of the light modality or modalities. A second modality, whole body therapeutic modality, can also reduce stress in the individual and provide calming effects, among others, wherein the therapeutic modality is applied several times from head to toe, as further described below.

A light modality, in preferred embodiments, may be used, and in some embodiments, may be a coherent light, non-coherent light, laser, light from the visible spectrum, such as red light or green light, and light from the infrared spectrum, such as infrared light. In preferred embodiments, a plurality of light modalities may be selected, or at least one, and in one embodiment, red light, green light, and infrared light may be selected. The red, green, and infrared light may be modalities of about either 630 or 660 nanometer wavelength for the red light, of about 574 nanometer wavelength for the green light, and of about 880 nanometer wavelength for the infrared light, in a preferred selection of light modalities found to provide preferred results from the therapy disclosed in the present invention. The light modalities may have intensities of about 6000 millicandela corresponding to the 630 or 660 nanometer wavelength, of about 370 millicandela corresponding to the 574 nanometer wavelength, and of about 4.2 milliwatts corresponding to the 880 nanometer wavelength. The term "about" when used regarding nanometers means within a range of plus or minus 50 nanometers, and when used regarding millicandella means within a range of plus or minus 100 millicandella, and regarding milliwatts means within a range of plus or minus 0.5 milliwatts.

Next, and in accordance with one embodiment, as graphically represented in FIG. 1, a therapeutic modality may be applied (20) to the therapeutic system of the body, and in preferred embodiments as mentioned above, a therapeutic light modality or a plurality of light modalities. In some preferred embodiments, the therapeutic modality or plurality of modalities, for example one or a plurality of light modalities, may be applied to a plurality of therapeutic systems of the body of the individual under treatment. Other therapeutic modalities may be used as described above. One preferred embodiment of the present invention may provide application of a plurality of modalities comprising at least one visible light modality and an infrared light modality, applied to at least one therapeutic microsystem of the individual. Therapeutic modalities may be further applied to at least one or a plurality of therapeutic microsystems, therapeutic microsystems being further described below.

A therapeutic system may be understood in the present disclosure to provide a set of therapeutic points, and potentially representative therapeutic points, that are representative of a body part or bodily area or portion thereof, or the body or substantial portion thereof. The therapeutic points may consist of a plurality of reflexology points, and in some embodiments, a plurality of therapeutic points such as acupressure points, acupuncture points, and meridian points. In accordance with some preferred embodiments, at least one or a plurality of therapeutic microsystems of the individual may be used in therapy of the present invention. A therapeutic microsystem may be understood in the present invention as a therapeutic system of therapeutic points representative of the body.

One preferred method of treatment may provide applying a therapeutic modality, at least one modality, or a plurality of modalities, to one or a plurality of therapeutic systems or microsystems selected from the ear, hand, and foot, and including meridian systems. Additional embodiments may provide application of the modality or modalities to systems of each of the ear, hand and foot, and in preferred embodiments, to systems or microsystems of each of the ears, hands and feet. Application of the modalities may occur preferably for one minute, and potentially on a pulse setting of 8 hertz, as more particularly described below. Application to the ear, hand or foot, or a respective two of each, may be particularly directed to the palm or palms of the hand or hands, and the sole or soles of the foot or feet, respectively. Application of the modality or modalities may be particularly directed to a meridian system, and wherein at least one or a plurality of meridians of the system may be unblocked through the therapeutical treatment of the present invention, including modalities directed to the ear, hand or foot, or plurality thereof, respectively.

A preferred embodiment may also provide an oscillation or otherwise pulsing of the applied modality or modalities, and in embodiments providing light modalities such as red light, green light, and infrared light, oscillating or otherwise pulsing the modality or modalities at a frequency. The frequency may preferably be selected from a frequency range of about 8 hertz to about 5000 hertz or more, and some embodiments may even provide oscillation of the modality or modalities in a frequency sweep or otherwise changing oscillation or pulsing from about 8 hertz to about 5000 hertz or more. The inventors have found particular benefit in therapeutic treatment in accordance with the embodiments of the present invention utilizing the 8 hertz rate, potentially referred to as the low hertz rate, the Theta or Dolphin brain wave state, and Flicker Fusion Phenomenon in the relevant art. It is suggested that such low hertz oscillation rate may enhance relaxation and alleviate stress, among other benefits.

A further step in accordance with one embodiment, and as represented in FIG. 1, may provide the step of stimulating therapeutic points (30) of one or a plurality of therapeutic systems, and in some embodiments, stimulating a plurality of therapeutic points, as previously described, potentially of at least one or a plurality of therapeutic microsystems. In some preferred embodiments, stimulation may be provided to a plurality of therapeutic points, points that in some embodiments are of a plurality of therapeutic systems, that may be further representative of the body, as previously described. The stimulation provided in the present invention may be considered a departure from conventional systems in that treatment and application to a therapeutic system or systems, and in some preferred embodiments to therapeutic microsystems, may provide a more therapeutically encompassing treatment for an individual's body. Stimulation of therapeutic points in accordance with the present invention may occur after the application of the therapeutic modality or modalities and in accordance with the particular modality or modalities used, as is commonly known in the relevant arts. A subsequent step in accordance with some embodiments may provide therapeutically treating (40) the body or individual in response to the stimulation of therapeutic points. The body may respond to the stimulation, and further treatment may occur accordingly in response to the stimulation of therapeutic points, and may include known treatment in the relevant arts, including further application of therapeutic modalities and therapies, including therapies of acupuncture, acupressure, and reflexology.

Figure 2:
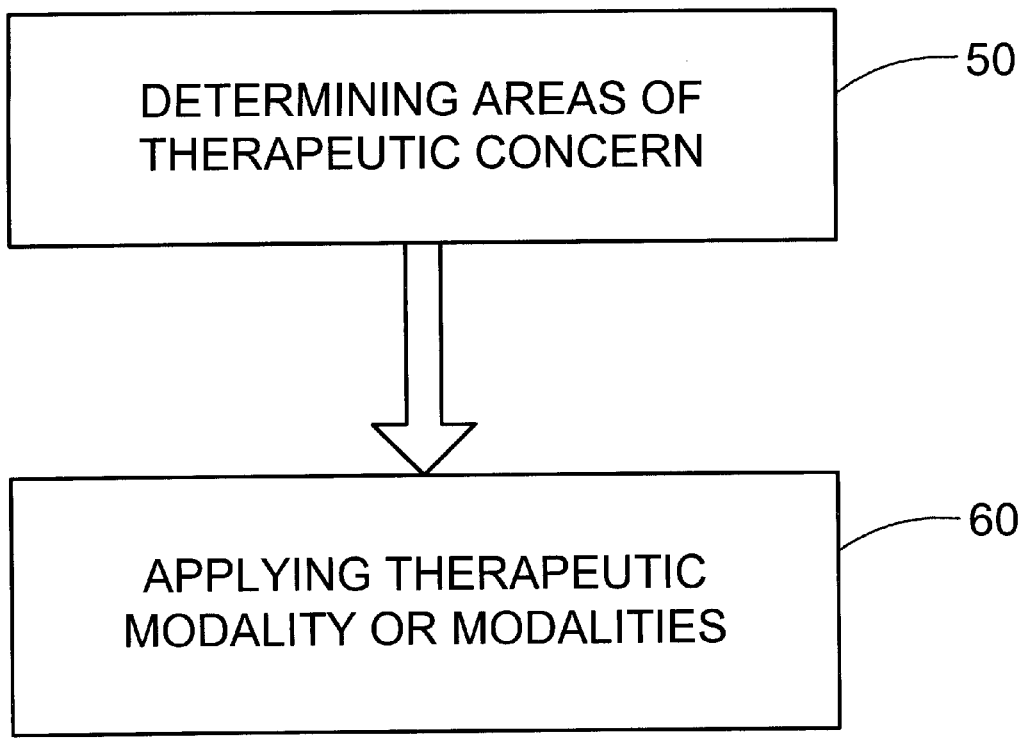
FIG. 2 is a diagrammatic representation of another embodiment of the present invention.

In accordance with some embodiments of the present invention, therapeutic treatment may be conducted, and in some embodiments, as further steps of previously described embodiments. One such treatment in accordance with the present invention is represented in FIG. 2. The therapeutic treatment may further comprise the step of determining at least one or a plurality of areas of therapeutic concern (50). Such determination may occur through traditional therapies and therapeutic modalities, or may be determined through the embodiments and steps of the invention, as previously described. The therapeutic modality or modalities that have been provided in accordance with embodiments herein may further provide treatment of which the area or areas of therapeutic concern may respond, or additional application of therapeutic modality or modalities may be provided to treat the area or areas. The application of therapeutic modality or modalities may be provided either directly to the area or areas of concern, or to therapeutic systems and microsystems representative of the area or areas. Applying therapeutic modality or modalities for such areas is represented in FIG. 2 as step (60). The step of determining area or areas of therapeutic concern may, in some embodiments, be provided as a determination of a blocked meridian or meridians, a determination of at least one or a plurality of injured areas, and an area or areas such as a muscle relaxation area, muscle pain area, joint pain area, muscle spasm, stiffness, arthritis, abdomen area, and area of the colic valve.

The embodiments of the present invention directed to method or process of therapeutic treatment may be accomplished by a therapeutic treatment system or device that provides for a stated function or step as provided in the method or process of therapeutic treatment embodiments disclosed herein as the present invention. Such treatment systems or devices may include modality elements, such as light emitting elements, and in preferred embodiments light emitting diodes (LEDs), modality elements that are juxtaposed or otherwise configured to provide modality application not only to particular therapeutic points as previously described, but further to provide modality application to one or a plurality of therapeutic systems, and in preferred embodiments, therapeutic microsystems. Power and control elements may further be provided in accordance with the present invention to provide novel therapeutic treatment systems and devices.

Blood irradiation by LED 630–800 nm causes a photochemical reaction in the blood, which is particularly useful for strengthening the immune system of the body. Therefore, placement of the LES's on the body over blood vessels, especially in areas where the blood vessels are close to the skin surface, is effective to irradiate the blood and therefore to oxygenate and improve the characteristics of the blood, including vasodilation, peripheral circulation, bactericidal and viricital effects. This reaction carries into the capillary network stimulating blood cells, improving and recovering physiological functions. As shown in physiological and physiochemical tests, this LED irradiation technology can rapidly alter the flow conditions of blood and oxygen in the body. From increased microcirculation, strengthened blood cells, increased cell metabolisma, increased immune system functions, and faster tissue regeneration this technology is very beneficial to the total functional parameters of the human body.

As can be understood from the foregoing, the basic concepts of the present invention may be embodied in a variety of ways. It involves both therapeutic treatment techniques as well as devices to accomplish appropriate treatment. In this application, the therapeutic treatment techniques are explicitly disclosed and devices or systems pertaining to such techniques, to achieve the various techniques described and as inherent to application or utilization of the disclosed therapeutic techniques. They are simply the natural result of conducting the therapeutic techniques as intended and described. In addition, while some methods and processes are disclosed, it should be understood that these not only may be accomplished with certain systems or devices, but also can be varied in a number of ways. Importantly, as to all of the foregoing, all of these facets should be understood to be encompassed and enabled by this disclosure.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled.

As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of an "modality element" should be understood to encompass disclosure of the provision of modality or modalities,—whether explicitly discussed or not—and, conversely, were there only disclosure of the act of providing modality or modalities, such a disclosure should be understood to encompass disclosure of a "modality element" and even a means for providing modality or modalities. Such changes and alternative terms are to be understood to be explicitly included in the description. In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

The disclosed embodiments of the invention claimed herein are:

1. A method of therapeutic treatment of the body of an individual, comprising:
   a. applying a therapeutic modality to a therapeutic microsystem of each of the ear, hand, and foot;
   b. stimulating a plurality of therapeutic points of said therapeutic microsystems; and
   c. therapeutically treating said body in response to said stimulating.

2. A method of therapeutic treatment of the body of an individual as described in claim 1, wherein said stimulating comprises stimulating a plurality of reflexology points.

3. A method of therapeutic treatment of the body of an individual as described in claim 1 wherein said stimulating comprises stimulating a plurality of therapeutic points selected from a group consisting of acupressure points, acupuncture points, or meridian points.

4. A method of therapeutic treatment of the body of an individual as described in claim 1 including applying the modality for features selected from the group consisting of abdomen, a colic valve, and whole body.

5. A method of therapeutic treatment of the body of an individual as described in claim 1 wherein said applying comprises applying a therapeutic modality to a therapeutic microsystem of each of the ears, hands and feet.

6. A method of therapeutic treatment of the body of an individual as described in claim 5 wherein said applying comprises applying a therapeutic modality for at least about one minute to a therapeutic microsystem of each of the ears, hands and feet.

7. A method of therapeutic treatment of the body of an individual as described in claim 6 wherein said applying comprises applying a therapeutic modality to the palms of each of said hands and the soles of each of said feet.

8. A method of therapeutic treatment of the body of an individual as described in claims 1, 4 or 5 wherein said applying comprises applying a therapeutic modality to a meridian system.

9. A method of therapeutic treatment of the body of an individual as described in claim 8 wherein said therapeutically treating comprises unblocking at least one meridian of said meridian system.

10. A method of therapeutic treatment of the body of an individual as described in claim 1, further comprising the steps of determining at least one area of therapeutic concern and applying a therapeutic modality to said determined at least one area of therapeutic concern.

11. A method of therapeutic treatment of the body of an individual as described in claim 1, further comprising the step of determining at least one area of therapeutic concern and wherein said step of applying a therapeutic modality further comprises applying a therapeutic modality to which said determined at least one area of therapeutic concern is responsive.

12. A method of therapeutic treatment of the body of an individual as described in claim 11 wherein said step of applying a therapeutic modality comprises applying a therapeutic modality to said at least one area of therapeutic concern.

13. A method of therapeutic treatment of the body of an individual as described in claim 11 wherein said step of determining at least one area of therapeutic concern comprises determining at least one blocked meridian.

14. A method of therapeutic treatment of the body of an individual as described in claim 11 wherein said step of determining at least one area of therapeutic concern comprises determining at least one injured area of said body.

15. A method of therapeutic treatment of the body of an individual as described in claim 11 wherein said step of determining at least one area of therapeutic concern comprises determining at least one area of said body selected from the group consisting of a muscle relaxation area, muscle pain area, joint pain area, muscle spasm, stiffness, arthritis, abdomen area, and a area of the colic valve.

16. A method of therapeutic treatment of the body of an individual as described in claim 1, wherein said applying a therapeutic modality comprises applying at least one light modality.

17. A method of therapeutic treatment of the body of an individual as described in claim 16, wherein said applying a therapeutic modality comprises applying therapeutic modalities selected from the group consisting of coherent light, non-coherent light, laser, red light, green light and infrared light.

18. A method of therapeutic treatment of the body of an individual as described in claim 16, wherein said applying a therapeutic modality comprises applying modalities of red light, green light and infrared light.

19. A method of therapeutic treatment of the body of an individual as described in claim 18, wherein said modalities are of about either 630 or 660 nanometer wavelength for said red light, of about 574 nanometer wavelength for said green light, and of about 880 nanometer wavelength for said infrared light.

20. A method of therapeutic treatment of the body of an individual as described in claim 19, wherein said modalities have light intensities of about 6000 millicandela corresponding to of about a 630 or 660 nanometer wavelength, of about 370 millicandela corresponding to of about a 574 nanometer wavelength, and of about 4.2 milliwatts corresponding to of about a 880 nanometer wavelength.

21. A method of therapeutic treatment of the body of an individual as described in claim 18, further comprising the step of oscillating said modalities of red light, green light and said infrared light at a frequency selected from a frequency range of about 8 hertz to about 5000 hertz or more.

22. A method of therapeutic treatment of the body of an individual as described in claim 18, further comprising the step of oscillating said modalities of red light, green light and said infrared light in a frequency sweep from about 8 hertz to about 5000 hertz or more.

23. A method of therapeutic treatment of an individual comprising:
   a. applying a therapeutic modality comprising red, green, and infrared light to a plurality of therapeutic systems of said individual;
   b. stimulating a plurality of therapeutic points of each said plurality of therapeutic systems; and
   c. therapeutically treating said individual in response to said stimulating.

24. A method of therapeutic treatment of an individual as described in claim 23, wherein said stimulating comprises stimulating a plurality of reflexology points.

25. A method of therapeutic treatment of an individual as described in claim 23, wherein said stimulating comprises stimulating a plurality of therapeutic points selected from the group consisting of acupressure points, acupuncture points, and meridian points.

26. A method of therapeutic treatment of an individual as described in claim 25, wherein at least one plurality of therapeutic points of said plurality of therapeutic systems is representative of the body of said individual.

27. A method of therapeutic treatment of an individual as described in claim 23, wherein said applying comprises applying the modality for features selected from the group consisting of abdomen, a colic valve, and whole body.

28. A method of therapeutic treatment of an individual as described in claim 23, including applying said therapeutic modality to each of a plurality of therapeutic microsystems of said individual.

29. A method of therapeutic treatment of an individual as described in claim 28, including applying said therapeutic modality to each of a plurality of therapeutic microsystems selected from the group consisting of a ear, hand, and foot.

30. A method of therapeutic treatment of an individual as described in claim 28, including applying said therapeutic modality to at least one therapeutic microsystem of each of the ear, hand and foot.

31. A method of therapeutic treatment of an individual as described in claim 28, including applying said therapeutic light modality to at least one therapeutic microsystem of each of the ears, hands and feet.

32. A method of therapeutic treatment of an individual as described in claim 31, including applying said therapeutic modality for at least about one minute to at least one therapeutic microsystem of each of the ears, hands and feet.

33. A method of therapeutic treatment of an individual as described in claim 32, including applying said therapeutic modality to a palm of each of said hands and a sole of each of said feet.

34. A method of therapeutic treatment of an individual as described in claim 23, including applying said therapeutic modality to a meridian system.

35. A method of therapeutic treatment of an individual as described in claim 34, wherein said step of therapeutically treating comprises unblocking at least one meridian of said meridian system.

36. A method of therapeutic treatment of an individual as described in claim 25, 27, 28, or 31 further comprising determining at least one area of therapeutic concern and applying said therapeutic modality to such at least one area of therapeutic concern.

37. A method of therapeutic treatment of an individual as described in claim 23, further comprising determining at least one area of therapeutic concern and applying said therapeutic modality to such area of therapeutic concern that is responsive to at least one of said red, green, and infrared light.

38. A method of therapeutic treatment of an individual as described in claim 37, including applying said therapeutic modality to said at least one area of therapeutic concern.

39. A method of therapeutic treatment of an individual as described in claim 37, wherein said determining at least one area of therapeutic concern comprises determining at least one blocked meridian.

40. A method of therapeutic treatment of an individual as described in claim 37, wherein said determining at least one area of therapeutic concern comprises determining at least one injured area of said body.

41. A method of therapeutic treatment of an individual as described in claim 37, wherein said determining at least one area of therapeutic concern comprises determining at least one area of said body selected from the group consisting of a musole relaxation area, muscle pain area, joint pain area, muscle spasm, stiffness, arthritis, abdomen area, and a area of the colic valve.

42. A method of therapeutic treatment of an individual as described in claim 23, further comprising oscillating said modalities of red light, green light and said infrared light at a frequency selected from a frequency range of about 8 hertz to about 5000 hertz or more.

43. A method of therapeutic treatment of an individual as described in claim 23, wherein said modalities are of about either 630 or 660 nanometer wavelength for said red light, of about 574 nanometer wavelength for said green light, and of about 880 nanometer wavelength for said infrared light.

44. A method of therapeutic treatment of an individual as described in claim 43, wherein said modalities have light intensities of about 6000 millicandela corresponding to of about either a 630 or 660 nanometer wavelength, of about 370 millicandela corresponding to of about a 574 nanometer wavelength, and of about 4.2 milliwatts corresponding to 880 nanometer wavelength.

45. A method of therapeutic treatment of an individual as described in claim 25, further comprising oscillating said modalities of red light, green light and said infrared light in a frequency sweep from about 8 hertz to about 5000 hertz or more.

46. A method of therapeutic treatment of an individual, comprising:
   a. applying a plurality of therapeutic modalities comprising at least one visible light modality and an infrared light modality to at least one therapeutic microsystem of each of an ear, a hand, and a foot of said individual;
   b. stimulating a plurality of therapeutic points of said at least one therapeutic microsystem; and
   c. therapeutically treating said individual in response to said step of stimulating.

47. A method of therapeutic treatment of an individual as described in claim 46, including applying the therapeutic modalities to at least one of the group consisting of abdomen, a colic valve, and whole body therapeutic modality.

48. A method of therapeutic treatment of an individual as described in claim 46, including applying the plurality of therapeutic modalities to at least one therapeutic microsystem of each of the ears, hands and feet.

49. A method of therapeutic treatment of an individual as described in claim 48, including applying the plurality of therapeutic modalities for at least about one minute to at least one therapeutic microsystem of each of the ears, hands and feet.

50. A method of therapeutic treatment of an individual as described in claim 49, including applying the plurality of therapeutic modalities to a palm of each of said hands and to a sole of each of said feet.

51. A method of therapeutic treatment of an individual as described in claim 46, further comprising determining at least one area of therapeutic concern and applying the therapeutic modality to such at least one area of therapeutic concern.

52. A method of therapeutic treatment of an individual as described in claim 46, further comprising determining at least one area of therapeutic concern and applying the therapeutic modality to such area of therapeutic concern that is responsive to at least one of said red, green, and infrared light.

53. A method of therapeutic treatment of an individual as described in claim 46, including applying the plurality of therapeutic modalities to said at least one area of therapeutic concern.

54. A method of therapeutic treatment of an individual as described in claim 52, wherein said determining at least one area of therapeutic concern comprises determining at least one blocked meridian.

55. A method of therapeutic treatment of an individual as described in claim 52, wherein said determining at least one area of therapeutic concern comprises determining at least one injured area of said body.

56. A method of therapeutic treatment of an individual as described in claim 52, wherein said determining at least one area of therapeutic concern comprises determining at least one area of said body selected from the group consisting of a muscle relaxation area, muscle pain area, joint pain area, muscle spasm, stiffness, arthritis, abdomen area, and a area of the colic valve.

57. A method of therapeutic treatment of an individual as described in claim 46, wherein said at least one visible light modality comprises a red light and a green light and said infrared light modality comprises infrared light.

58. A method of therapeutic treatment of an individual as described in claim 57, wherein said modalities are of about either 630 or 660 nanometer wavelength for said red light, of about 574 nanometer wavelength for said green light, and of about 880 nanometer wavelength for said infrared light.

59. A method of therapeutic treatment of an individual as described in claim 58, wherein said modalities have light intensities of about 6000 millicandela corresponding to of about either a 630 or 660 nanometer wavelength, of about 370 millicandela corresponding to of about a 574 nanometer wavelength, and of about 4.2 milliwatts corresponding to 880 nanometer wavelength.

60. A method of therapeutic treatment of an individual as described in claim 57, further comprising the step of oscillating said modalities of red light, green light and said infrared light at a frequency selected from a frequency range of about 8 hertz to about 5000 hertz or more.

61. A method of therapeutic treatment of an individual as described in claim 57, further comprising the step of oscillating said modalities of red light, green light and said infrared light in a frequency sweep from about 8 hertz to about 5000 hertz or more.

62. A method of therapeutic treatment of the body of an individual, comprising:
   a. applying a therapeutic modality comprising red light, green light, and infrared light to a plurality of therapeutic systems of said body;
   b. stimulating a plurality of therapeutic points of said plurality of therapeutic systems representative of said body; and c. therapeutically treating said body in response to said stimulating.

63. A method of therapeutic treatment of the body of an individual, comprising:
   a. applying a therapeutic modality comprising green light to a plurality of therapeutic systems of said body;
   b. stimulating a plurality of therapeutic points of said plurality of therapeutic systems representative of said body; and
   c. therapeutically treating said body in response to said stimulating.

64. A method of therapeutic treatment of an individual, comprising the steps of:
   a. applying at least one therapeutic light modality to at least one therapeutic microsystem of each of an ear, a hand, and a foot of said individual;
   b. stimulating a plurality of therapeutic points of each said plurality of therapeutic systems; and
   c. therapeutically treating said individual in response to said step of stimulating.

65. A method of therapeutic treatment of an individual, comprising:
   a. applying a plurality of therapeutic modalities comprising at least a red light modality, a green light modality and an infrared light modality to at least one therapeutic microsystem of said individual;
   b. stimulating a plurality of therapeutic points of said at least one therapeutic microsystem; and
   c. therapeutically treating said individual in response to said step of stimulating.

66. A method of therapeutic treatment of an individual, comprising:
   a. applying a plurality of therapeutic modalities comprising at least a green light modality and an infrared light modality to at least one therapeutic microsystem of said individual;
   b. stimulating a plurality of therapeutic points of said at least one therapeutic microsystem; and
   c. therapeutically treating said individual in response to said step of stimulating.

* * * * *